United States Patent
Neda et al.

(10) Patent No.: US 6,879,385 B2
(45) Date of Patent: Apr. 12, 2005

(54) NONDESTRUCTIVE READING METHOD FOR ISOTOPIC LABEL

(75) Inventors: Tokudai Neda, Tokyo (JP); Yasuharu Yokoi, Tokyo (JP); Kenji Maeda, Tokyo (JP); Kenji Horiuchi, Tokyo (JP); Satoshi Yamashita, Tokyo (JP)

(73) Assignee: Tokyo Gas Co., Ltd., Tokyo (JP)

( * ) Notice: Subject to any disclaimer, the term of this patent is extended or adjusted under 35 U.S.C. 154(b) by 21 days.

(21) Appl. No.: 10/380,248

(22) PCT Filed: Oct. 4, 2001

(86) PCT No.: PCT/JP01/08757

§ 371 (c)(1),
(2), (4) Date: Mar. 11, 2003

(87) PCT Pub. No.: WO02/29705

PCT Pub. Date: Apr. 11, 2002

(65) Prior Publication Data

US 2003/0178561 A1 Sep. 25, 2003

(30) Foreign Application Priority Data

Oct. 4, 2000 (JP) .................................. 2000-305568

(51) Int. Cl.[7] .................................................. G06K 9/74
(52) U.S. Cl. ....................................................... 356/71
(58) Field of Search ........................ 356/71, 300, 319, 356/326, 432–435; 382/135–140

(56) References Cited

U.S. PATENT DOCUMENTS

| 5,760,394 | A |   | 6/1998  | Welle |
| 6,008,888 | A | * | 12/1999 | Nottke et al. .................. 356/71 |
| 6,108,082 | A | * | 8/2000  | Pettipiece et al. .......... 356/301 |
| 6,473,165 | B1| * | 10/2002 | Coombs et al. ............... 356/71 |

FOREIGN PATENT DOCUMENTS

| JP | 7-503541   | 4/1995  |
| JP | 10-88180   | 4/1998  |
| JP | 10-504112  | 4/1998  |
| JP | 10-287075  | 10/1998 |
| JP | 11-316200  | 11/1999 |
| JP | 2000-43460 | 2/2000  |
| WO | WO 97/43751| 11/1997 |

* cited by examiner

*Primary Examiner*—Michael P. Stafira
(74) *Attorney, Agent, or Firm*—Flynn, Thiel, Boutell & Tanis, P.C.

(57) ABSTRACT

A nondestructive reading method for an isotopic label, capable of easily and quickly reading information on an isotopic label imparted to an article in advance without destroying the label, and a nondestructive reading-use isotopic label suitably using this method. In addition, information obtained by this nondestructive reading method is used to easily and quickly judge the authenticity of an article.

28 Claims, 10 Drawing Sheets

CASE OF A DIFFUSE REFLECTION METHOD

CODING EXAMPLE 1

CODING EXAMPLE 2

| SUBSTANCE M1 HAVING A CONTENT RATIO OF ISOTOPE X1 OF CONSTITUENT ELEMENT X SIGNIFICANTLY HIGHER THAN A CONTENT RATIO OF X2

| SUBSTANCE M2 HAVING A CONTENT RATIO OF ISOTOPE X1 OF CONSTITUENT ELEMENT X SIGNIFICANTLY LOWER THAN A CONTENT RATIO OF X2

| MIXTURE M3 OF SUBSTANCE M1 AND SUBSTANCE M2 SUBSTANTIALLY IN EQUAL AMOUNTS

| NIL

CASE OF A DIFFUSE REFLECTION METHOD

CASE OF AN ATTENUATED TOTAL REFLECTION METHOD (ATR METHOD)

CASE OF AN INFRARED ABSORPTION METHOD
USING A SEMICONDUCTOR LASER

CASE OF A RAMAN SCATTERING METHOD
USING A SEMICONDUCTOR LASER

NONDESTRUCTIVE READING METHOD FOR ISOTOPIC LABEL

TECHNICAL FIELD

This invention relates to a method for reading an isotopic label which has been attached to an article beforehand and is difficult to forge and falsify, a method for judging the authenticity of an article using the information obtained by the reading method, and an isotopic label adapted for use in these methods.

TECHNICAL BACKGROUND

An anti-counterfeit method of articles has been proposed wherein a substance that is so controlled as to have a content ratio of a stable isotope different from the natural isotopic abundance ratio is employed as a label. For instance, in Japanese Laid-open Patent Application No.H10-287075, assigned to the present applicant, it is proposed that a label or code whose content ratio of $^{13}C$ is made larger than a natural isotopic value is used. In Japanese Laid-open Patent Application No.H11-316200, a method of identifying a vehicle or television receiver susceptible to theft is proposed, in which although the content ratio of a stable isotope is not controlled, at least two types of substances including carbon-cage molecules such as of $C_{60}$ or the like and a substance having a characteristic spectrum such as a metallo-organic soap are used as a label after control of a ratio and concentrations. However, the Japanese Laid-open Patent Application No. H11-316200 makes little mention of specific labeled substances, or any reading method is not particularly proposed. The Japanese Laid-open Patent Application No. 2000-43460, assigned to the present applicant, proposes the use of a label or code made of $C_{60}$ wherein a content ratio of $^{13}C$ is set at a value different from the natural value in order that the difference in degree of splitting of a light absorption spectrum of $C_{60}$ is utilized. Although this code is very effective in anti-counterfeiting thereof, limitation is placed on the range of application when using $C_{60}$ alone. Accordingly, there is a demand for development of various types of labeled substances.

Additionally, WO 97/43751 (U.S. Pat. No. 5,760,394) has proposed a labeling method using a substance wherein a stable isotope is controlled in content ratio thereof, and also a label. However, the measurement of the label and its identification are described in examples using only inductive couple plasma mass spectrometry (ICPMS) for the analysis. ICPMS is such that an element is quantitatively determined by measuring the intensity of an emission line corresponding to a wavelength of a photon which is discharged when a thermally excited atom or ion is returned to a lower energy level. Hence, in order to carry out the measurement using ICPMS, a solid or liquid sample has to be initially destroyed thereby causing free atoms to be generated. In this way, ICPMS requires not only such a large-scale apparatus per se as a mass spectrometer, but also the essential step of generating free atoms by destroying a solid or liquid sample, thus presenting a serious problem in terms of usefulness.

It should be noted that with respect to the reading of the label, mention is made merely of a suitable means only at the Abstract of the patent, and no other reading means is disclosed in the specification only with the statement concerning the above-mentioned ICPMS, and that any disclosure is not found at all particularly with respect to a nondestructive method. In addition, although the WO 97/43751 enumerates a great number of elements that are able to change a content ratio of a stable isotope for use as a label, how these elements are used as constituent elements for what types of substances are not illustrated except that mention is made only of $Nd_2O_3$ and $Dy_2O_3$ in examples. In view of this, it is nothing else that further studies and developments are necessary with respect to how these elements are usable as constituent elements of what types of substances.

Accordingly, a difficulty is involved in the practical use of ICPMS which is based on the assumption that a sample is destroyed, i.e. a label is destroyed as set out in the examples of WO 97/43751. Consequently, further studies and developments toward the practical use are necessary so that the information of a label can be obtained as it stands, if possible, or can be obtained nondestructively. More particularly, the development of a technique is strongly desired that the label be not destroyed, but information thereof is read as it is, ensuring immediate application to judgment on the authenticity of an article.

The invention has been accomplished in order to solve the problems involved in the prior art methods using an isotopic label and has for its object the provision of a method for readily and reliably reading an isotopic label, attached on an article beforehand, without destroying the label and a method for judging the authenticity of an article using the information obtained by the reading method, and also the provision of a novel and useful isotopic label which is adapted for use in the reading and authenticity judging methods.

DISCLOSURE OF THE INVENTION

In the practice of the invention, an isotopic label is attached on an article beforehand. The isotopic label is made of substances which, respectively, have a plurality of stable isotopes of at least one element selected among elements constituting the substances, i.e. a constituent element, and which include both a substance wherein at least one stable isotope is so controlled that a content ratio thereof is lower than the natural isotopic abundance ratio (although both are same structurally, the content ratio of the stable isotope of the element is so controlled as to be not higher than the natural isotopic abundance ratio) and a substance wherein at least one stable isotope is so controlled that a content ratio thereof not lower than the natural isotopic abundance ratio (although both are structurally same, the content ratio of the stable isotope of the element is so controlled as to be not lower than the natural isotopic abundance ratio). Vibration spectra of the substances differ from a vibration spectrum of a substance having all content ratios of the stable isotopes of the constituent elements are equal to the natural isotopic abundance ratios, respectively. The invention is also favorable for nondestructively reading and obtaining the vibration spectra of the substances constituting the isotopic label.

Further, in the practice of the invention, an isotopic label is attached on an article beforehand wherein the isotopic label is made of a substance which has at least two elements selected from hydrogen, carbon, nitrogen and oxygen as the constituent elements with each of the content ratios of stable isotopes thereof being controlled to be different from the natural isotopic abundance ratio and which has a vibration spectrum different from the vibration spectrum of the substance whose content ratios of stable isotopes of the constituent elements are, respectively, equal to the natural isotopic abundance ratios. The invention is also favorable for nondestructively reading and obtaining the vibration spectrum of the substance constituting the isotopic label. In this case, it is favorable that an element or elements other than the above-mentioned elements and constituting the isotopically labeled substance do not have stable isotopes. If the other elements of the constituent elements of the isotopically labeled substance have stable isotopes, part of the effects expected from the elements whose the ratios of the stable isotopes have been controlled may be counteracted.

In the present specification, the label attached on an article beforehand and made of such a substance or substances as set forth hereinabove is called "isotopic label".

In the present invention, the information obtained according to the nondestructive reading method is utilized for a method of judging the authenticity of an article. More particularly, as stated hereinabove, the invention is also favorable for obtaining a vibration spectrum or spectra of the substance constituting the isotopic label nondestructively, and the thus obtained information is used to nondestructively judge the authenticity of the isotopic label-attached article. The authenticity judging method is carried out by use of a device of reading and obtaining vibration spectra, a device of reading an isotopic label through pattern recognition of data of vibration spectra, and a device of judging the authenticity of an article. In this case, these devices may be worked by connection via a communication network. For the communication network, at least one of a telephone communication network, an internet and an intranet can be used. Moreover, in order to perform the nondestructive authenticity judging method of an article, at least one of devices including a device of obtaining vibration spectra, a device of reading an isotopic label through pattern recognition of data of vibration spectra, and a device of judging the authenticity of an article may be controlled from a remote area, or control parameters may be designated from a remote area.

In addition, the invention provides isotopic labels of (1)~(3) below for nondestructive reading, which are adapted for use in a nondestructive reading method of the above-stated isotopic label and a method for judging the authenticity of an article.

(1) An isotopic label for nondestructive reading which is attached on an article beforehand, comprising substances constituting the isotopic label which, respectively, have at least one constituent element having a plurality of stable isotopes, include both a substance wherein a content ratio of at least one stable isotope of the constituent element is not higher than a natural isotopic abundance ratio and another substance wherein a content ratio of the stable isotope of the constituent element is not lower than a natural isotopic abundance ratio, and have vibration spectra differ from the vibration spectrum of the substance whose content ratios of stable isotopes of the constituent elements are equal to the natural isotopic abundance ratios, respectively.

(2) An isotopic label for nondestructive reading which is attached on an article beforehand, comprising a substance constituting the isotopic label which has at least two elements of constituent elements selected from hydrogen, carbon, nitrogen and oxygen with each of the content ratios of stable isotopes thereof controlled to be different from the natural isotopic abundance ratio and has a vibration spectrum different from the vibration spectrum of the substance whose content ratios of stable isotopes of the constituent elements are equal to the natural isotopic abundance ratios, respectively.

(3) An isotopic label for nondestructive reading which is attached on an article beforehand, comprising a substance constituting the isotopic label which has at least two elements of constituent elements selected from hydrogen, carbon, nitrogen and oxygen with each of the content ratios of stable isotopes thereof controlled to be different from the natural isotopic abundance ratio, wherein constituent elements other than hydrogen, carbon, nitrogen and oxygen are elements which has no stable isotopes and which has a vibration spectrum different from the vibration spectrum of the substance whose content ratios of stable isotopes of the constituent elements are equal to the natural isotopic abundance ratios, respectively.

EMBODIMENTS FOR CARRYING OUT THE INVENTION

Figure 1:
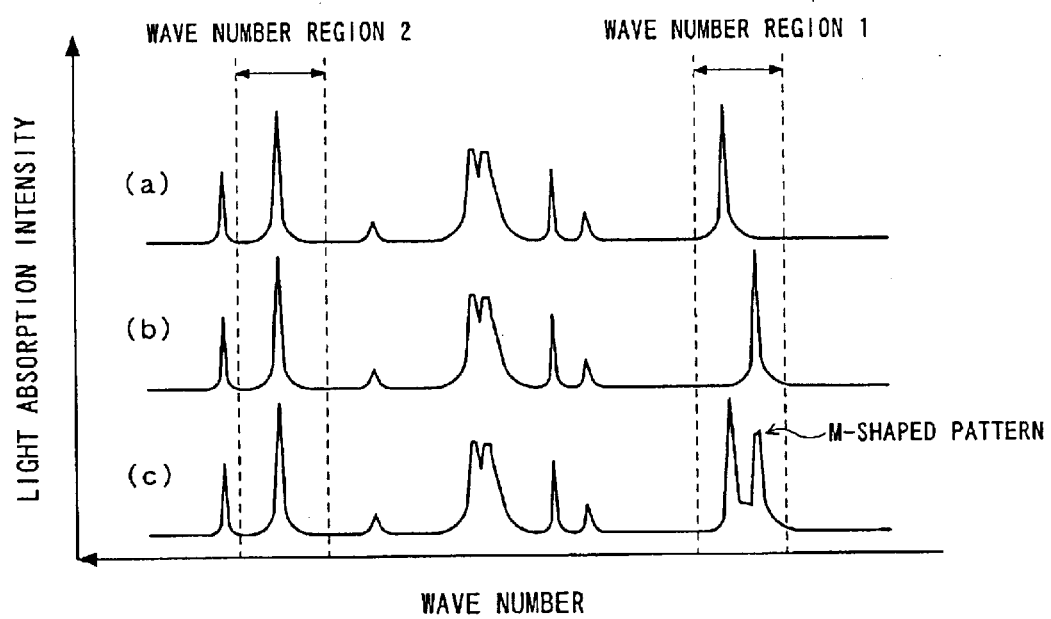
FIG. 1 is a view showing an outline of light absorption spectra of substances M1~M3 (a principle of nondestructive reading of an isotopic label)

In the practice of the invention, an isotopic label is attached on an article beforehand wherein the isotopic label is made of substances that have a plurality of stable isotopes of at least one element selected among constituent elements, include a substance in which at least one stable isotope is so controlled as to have a content ratio thereof is not higher than a natural isotopic abundance and a substance in which the at least one stable isotope has a content ratio thereof not lower than the natural isotopic abundance, and are used in combination, and wherein vibration spectra of the substances differ from a vibration spectrum of a substance having a content ratio of the stable isotope of the at least one element in coincidence with the natural isotopic abundance. The vibration spectra information of the labeled substances is nondestructively read and obtained as it is.

It should be noted here that both substances, i.e. a substance which has a plurality of stable isotopes with respect to at least one of constituent elements for the substance and has a controlled content ratio of at least one stable isotope thereof not higher than a natural isotopic abundance and a substance which has a controlled content ratio of the stable isotope not lower than the natural isotopic abundance, are structurally similar to each other and, respectively, have a content ratio of the stable isotope of the element different from the natural isotopic abundance.

It will be noted that the use, as a label, of a substance of the type wherein the constituent element of the isotopic label-constituting substance is carbon and the content ratio of $^{13}C$ is made larger than a natural value has been already developed (Japanese Laid-open Patent Application No. H10-287075). In contrast, according to the invention, in addition to a substance whose content ratio of $^{13}C$ is larger than a natural value, a substance whose content ratio of the stable isotope is not higher than a natural isotopic abundance is used in combination as stated hereinabove. This makes counterfeiting more difficult and can further increase a security level.

In the practice of the invention, a label made of an isotopic label constituting substance is attached on an article beforehand wherein constituent elements for the substance include at least two elements selected from hydrogen, carbon, nitrogen and oxygen, and the at least two elements are so controlled as to have content ratios of stable isotopes thereof different from natural isotopic abundances, respectively, so that the vibration spectrum thereof is made different from a vibration spectrum of a substance having content ratios of stable isotopes of these elements in coincidence with natural isotopic abundances. The vibration spectrum information of the isotopically labeled substance is read and obtained as it is, i.e., nondestructively.

In the case, when elements other than the above-indicated elements among the constituent elements of the isotopically labeled substance have stable isotopes, part of the effects expected from the elements which are controlled in the stable isotope ratio may be counteracted. In this sense, it is desirable that elements other than the above-mentioned constituent elements of the isotopically labeled substance do not have any stable isotope. Examples of the elements having no stable isotope include Be, F, Na, Al, P, Sc, Mn, Co, As, Y, Nb, Rh, I, Cs, Pr, Tb, Ho, Tm, Au, Bi, Th and the like.

In the practice of the invention, a vibration spectrum of a substance constituting an isotopic label is nondestructively obtained in a manner as set out hereinbefore, and the authenticity of the isotopic label-attached article is nondestructively judged based on the thus obtained information. Different types of isotopic labels made of such materials as described hereinabove may be built up in multiple layers and attached on the same portion of an article. Light is irradiated on the substances constituting the isotopic labels to identify the isotopic labels from the intensity of reflected light, of transmitted light or of scattered light thereby reading information thereof. In this way, the information of the isotopic labels can be utilized in high accuracy and quickly. In case where the invention is applied to the inspection of an anti-counterfeit, the information of the preliminarily attached isotopic label as set out before proves the article as authentic. If the information is not obtained, the article is judged as a counterfeit.

Thus, according to the invention, vibration spectra of an isotopic label can be read and obtained readily and accurately without destroying a sample or the isotopic label while permitting the isotopic label to stand, and the judgment of authenticity of an article attached with an isotopic label thereon can be made nondestructively, readily and accurately. In this regard, in the afore-indicated ICPMS (WO 97/43751), the step of destroying a solid or liquid sample, or an isotopic label to cause free atoms to be generated is essential, and such a large-scale apparatus as a mass spectroscope per se is necessary. According to the invention, the information on an isotopic label can be read nondestructively, readily and accurately, thus being very effective and useful from the standpoint of practical use.

Principle of Nondestructive Reading of an Isotopic Label

When light is irradiated on a substance to measure a ratio of absorbed light, the absorption ratio differs depending the energy of the irradiating light. The absorption ratio may be expressed by either absorbance or absorption intensity, and is illustrated in terms of absorbance hereinbelow. The results of the measurement are shown by a graph wherein the abscissa indicates a wave number or wavelength of irradiating light and the ordinate indicates an absorbance. This curve is called light absorption spectrum of the substance. The light transmittance spectrum or light reflection spectrum obtained by measuring a transmittance or reflectance in place of absorbance describes a light absorption spectrum-related curve, and thus illustration is made herein using the term of the light absorption spectrum on behalf of spectra including the last-mentioned ones.

In the light absorption spectrum, the reason why light is strongly absorbed at a specific energy (or at a specific wave number or specific wavelength) corresponding to a peak position is that when the energy level of an atom or molecule constituting a given substance is transferred to a higher level, an absorbed energy takes only a specific value.

With a molecule made of a plurality of atoms, vibrations take place between the atoms. The vibration energy of the molecule ascribed to the vibrations may take a specific value alone that is determined depending on the masses of individual atoms and the bonding force between the atoms. If a vibration state changes depending on the absorption of light, the value of the vibration energy changes. A possible value of the vibration energy is determined depending on the combination of vibrating atoms, and the energy of the light absorbed upon the change of the vibration energy is limited to a specific value.

Of light absorption spectra of a substance, a portion formed as a result of the change in vibration state between the constituent atoms is called vibration spectrum of the substance. The range of the irradiation light energy within which a vibration spectrum appears is usually limited to a portion called infrared region. The infrared region used herein is a general term for near infrared region, mid infrared region, and far infrared region. The light absorption spectrum is usually inherent to a given substance.

By the way, an isotope means the forms of an element having different atomic weights because of the difference in number of neutrons. Among isotopes, a stable isotope does not have radioactivity and is a stable one undergoing no decay. In a natural condition, the relative isotopic abundance ratio of individual elements is constant. For instance, carbon includes two isotopes of $^{12}C$ and $^{13}C$ and it is known that the natural isotopic abundance ratio of these isotopes is at 98.89:1.11. More particularly, with a substance wherein a content ratio of stable isotopes in an element constituting a substance having carbon as a constituent element is at the natural isotopic abundance ratio, the content ratio of $^{12}C$ relative to the total carbon content is at 98.89% and the content ratio of $^{13}C$ is at 1.11%.

The light absorption spectrum is usually inherent to a given substance, and the vibration energy between the constituent atoms of a substance depends on the masses of the atoms. The mass of an atom differs between the isotopes thereof. Accordingly, with a substance whose constituent element has stable isotopes, the content ratio of the stable isotopes influences the vibration spectrum. More particularly, the difference of the stable isotope content ratio of the constituent element of a substance from the natural isotopic abundance ratio results in the difference of the vibration spectrum.

In accordance with the invention, this phenomenon is utilized for nondestructive reading of an isotopic label. It will be noted that among light absorption spectra, a portion other than irradiation light where a vibration spectrum appears, such as a portion corresponding to a visible region, suffers little influence of the content ratio of stable isotopes.

For example, it is assumed that element X has two types of stable isotopes X1, X2 alone and substance M makes use of this element X as one of constituent elements thereof. The content ratios of stable isotopes of the constituent elements other than the constituent element X are coincident with natural isotopic abundance ratios, respectively. In this condition, a substance wherein the content ratio of the stable isotope X1 of the constituent element X is much higher than the content ratio of the isotope X2 is taken as M1, a substance wherein the content ratio of the stable isotope X1 of the constituent element X is much lower than the content ratio of the isotope X2 is taken as M2, and a substance made of a mixture of the substances M1 and M2 substantially in equal amounts is taken as M3.

In some case, the influence of the content ratio of these stable isotopes may clearly appear at part of the vibration spectra of these three kinds of substances M1, M2 and M3. FIG. 1 is a view showing the outlines of the light absorption spectra of the substances M1, M2 and M3, respectively. Since the content ratios of the stable isotopes of the element X constituting the molecule are different between the substances M1 and M2, a difference appears in the peak position within a wave number region 1 of the light absorption spectra shown in (a) and (b). With the light absorption spectrum (c) of the substance M3, a M-shaped peak appears as a result of the superposition of both peaks. When the light absorption spectrum at the wave number region is obtained, the substances M1~M3 can be identified, respectively. Depending on whether the ordinate of the graph is taken as an absorbance (absorption intensity) or as a transmittance (transmission intensity), the M-shaped peak may appear for the absorption intensity and the W-shaped peak appears for the transmission intensity. In this way, the substances M1~M3 can be, respectively, identified by obtaining light absorption spectra or light transmission spectra in the wave number region 1. It will be noted that the light absorption spectra in the wave number region 2 of FIG. 1 are common to the substances M1~M3.

If the state where the content ratio of the stable isotopes in the constituent element of the substance M is at the natural isotopic abundance is close to that of the substance M1, the other two types of substances M2, M3 cannot be obtained unless they are artificially synthesized by use of rare stable isotopes. Thus, these substances have rarity. When a label is constituted by use of such highly rare substances, it is realized to provide a label which is difficult to forge and is high in security level.

The case where the element X has two -types of stable isotopes X1, X2 has been illustrated hereinabove, which is true of the case where element X has three or more types of stable isotopes X1, X2, X3, . . . . In addition, it has been illustrated above that the content ratio of the stable isotopes of only one element X of constituent elements of a substance is controlled. The content ratios of stable isotopes of two or more, or at least two, elements selected among a plurality of constituent elements of a substance, such as hydrogen, carbon, nitrogen, oxygen and the like, may be controlled in a like manner. Moreover, with respect to at least two elements selected among a plurality of constituent elements of a substance, such as hydrogen, carbon, nitrogen, oxygen and the like, the stable isotope content ratios of the plural types of elements in the molecule of the substance may be likewise controlled, respectively.

Figure 2A:
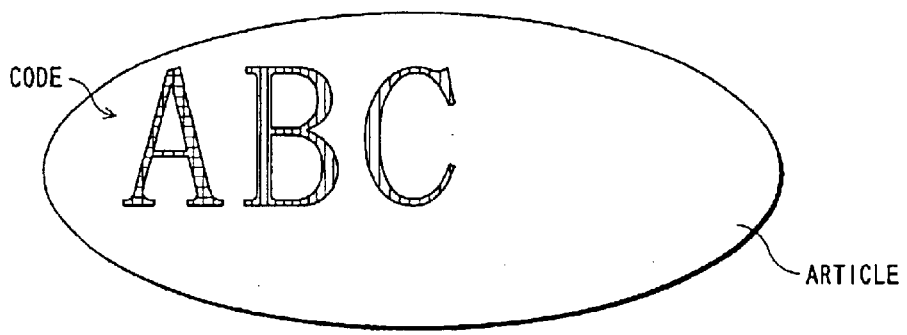
FIGS. 2(a) and 2(b) are a view showing examples of preliminarily attaching isotopic labels on articles for the purpose of anti-counterfeiting.
Figure 2B:
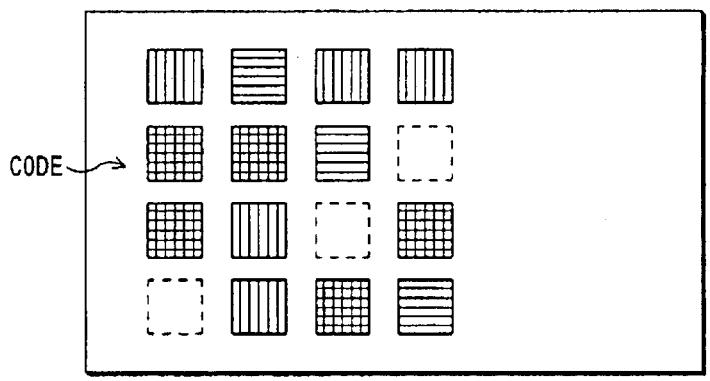

FIGS. 2(a) and 2(b) show an instance of attaching an isotopic label on an article beforehand for the purpose of anti-counterfeiting. In FIGS. 2(a) and 2(b), an isotopic label is indicated as a code herein and whenever it appears hereinafter in the drawings. In FIG. 2(b) shows an instance of an isotopic label where isotopic label-attaching spots are two-dimensionally arranged, i.e., an instance of attaching an isotopic label wherein 16 spots are attached with or not attached with any of substances M1~M3. When information is expressed in terms of whether any of the substances M1, M2 and M3 used for the isotopic label is attached to a spot or no substance is attached to the spot, four pieces of information per spot may be coded. Because any one of the four pieces of information can be assigned to one spot, the use of a label consisting of a substance controlled in the content ratio of the stable isotope at at least one spot enables one to express $4^{16}-2^{16}$=about 4.29 billions of pieces of information. According to this procedure, a label which is difficult to forge and has a high information recording density can be realized.

Nondestructive Reading Means of an Isotopic Label

In the practice of the invention, information on an isotopic label is nondestructively read by obtaining a vibration spectrum of a substance constituting the isotopic label. For the reading, an infrared absorption method or a Raman scattering method is conveniently used.

In the infrared absorption method, an infrared ray is irradiated on a substance constituting an isotopic label and the intensity of reflected light, transmitted light or scattered light is detected by means of a light-receiving element to obtain a vibration spectrum of the substance for the isotopic label. The vibration spectrum can be obtained by a diffuse reflection method, an attenuated total reflection method (ATR method), photoacoustic spectrometry and the like, which are ordinarily, widely employed IR absorption methods.

In the Raman scattering method, monochromatic light is irradiated on a substance for an isotopic label and the resultant Raman line appearing in the scattered light is detected by a light-receiving element to obtain a vibration spectrum of the substance of the isotopic label from the wave number (wavelength) or intensity.

When using a device of obtaining the vibration spectrum, various control parameters including the position of the isotopic label to be read on an article, the range of a wave number at which the vibration spectrum is to be obtained, and the like can be set appropriately.

Where the invention is applied to the judgment of the authenticity of an article (see Example 7), a smaller-size vibration spectrum-obtaining device is convenient for the purpose of accommodation and portability. In this case, it is favorable to use as a light source for irradiation light a device capable of conversion of continuous light into monochromatic light through an acousto-optic tunable filer (abbreviated as AOTF) or a semiconductor laser.

Figure 3:
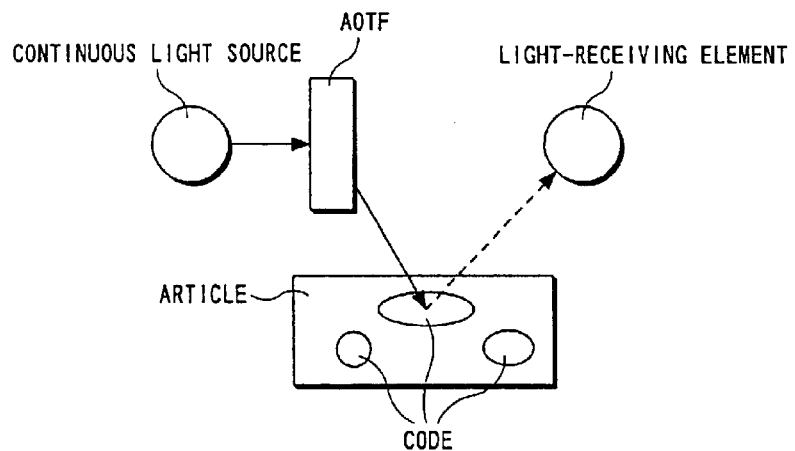
FIG. 3 a view showing an example where vibration spectra are obtained by a diffused reflection method using AOTF.
Figure 4:
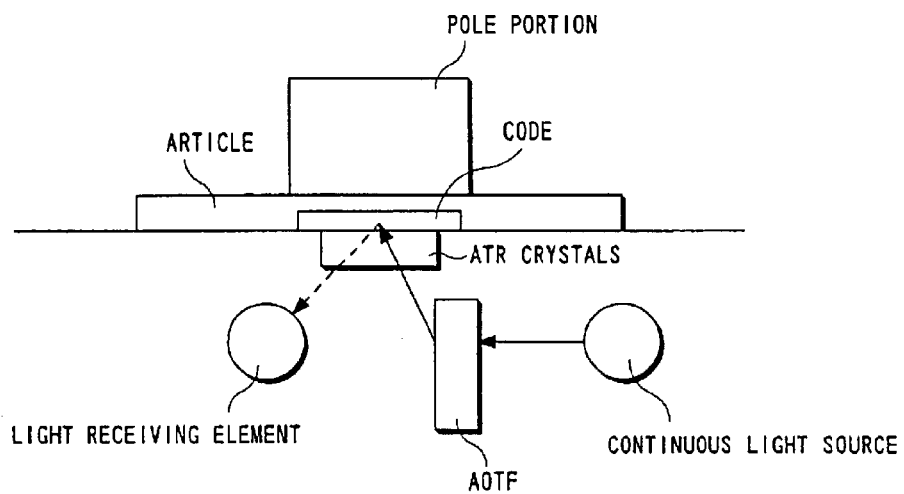
FIG. 4 is a view showing an example wherein vibration spectra are obtained by an attenuated total reflection method using AOTF.

When using AOTF, monochromatic light within a wide range of wave number (wavelength) can be created without any movable parts, so that the vibration spectrum-obtaining device can be made small in size and light in weight. FIG. 3 shows an instance where vibration spectra are obtained by a diffuse reflection method using AOTF. FIG. 4 shows an instance where vibration spectra are obtained by an attenuated total reflection method using AOTF.

Figure 5:
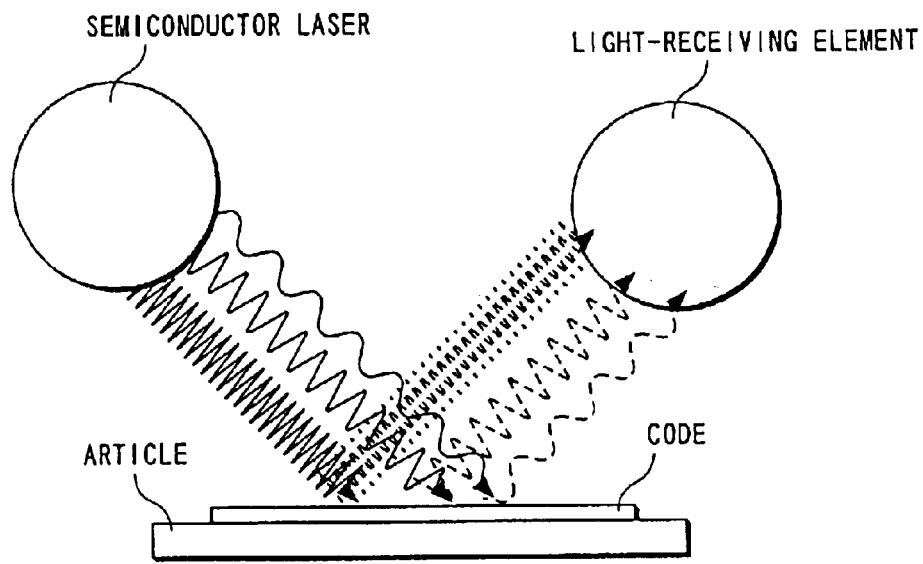
FIG. 5 is a view showing an example wherein a beam emitted from a semiconductor laser is irradiated on a substance constituting an isotopic label to measure an absorption intensity, a transmission intensity and a reflection intensity.
Figure 6:
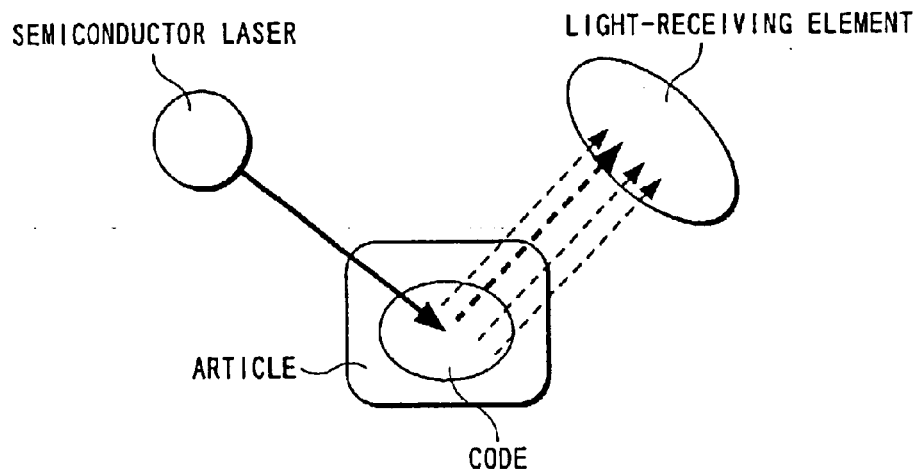
FIG. 6 is a view showing an example wherein light emitted from a semiconductor laser is irradiated on a substance constituting an isotopic label and Raman lines appearing in the resultant scattered light are detected with a light-receiving element to determine a vibration spectrum from the wave number (wavelength) and intensity thereof.

When using a semiconductor laser, monochromatic light can be created by use of a very small-sized light source. In order to obtain one peak (or valley) in the vibration spectrum, it becomes necessary to obtain spectral information with respect to three wave numbers (wavelengths) at which the intensity changes as being low→high→low (or high→low→high). In the infrared absorption method, as shown in FIG. 5, the light generated by a semiconductor laser is irradiated on a substance for a label to measure an absorption intensity, a transmission intensity or a reflection intensity. The wave number (wavelength) of the beam obtained from a light source using a semiconductor laser can be changed within a specified range by controlling the temperature of the semiconductor laser or an inputted current value, or by using an external resonator. This enables one to obtain at least one peak in the vibration spectrum by use of a semiconductor laser. In the Raman scattering method, as shown in FIG. 6, the beam generated by a semiconductor laser is irradiated on a substance for an isotopic label and a Raman line appearing in the resulting scattered light is detected by means of a light-receiving element to obtain a vibration spectrum from the wave number (wavelength) or intensity.

Although information concerning a content ratio of a stable isotope in the constituent element of a substance is obtained by obtaining a vibration spectrum of the substance for an isotopic label, information concerning the color of the substance can be obtained by obtaining a light absorption spectrum of the substance within a visible region. Using both pieces of information, the substance for an isotopic label is identified, thereby improving the reliability of the identification, thus enabling the isotopic label to maximize its latent security level.

When using substances such as dyes which have the same color but are different in the content ratio of stable isotopes, it becomes possible to provide isotopic labels which are difficult to discriminate through visual observation. In this connection, however, the discrimination through visual observation is not performed with the unmanned or unattended case such as of a vending machine. If a label is read only from a vibration spectrum, isotopic labels which have the same vibration spectrum but are different in color cannot be discriminated from each other. In the unmanned case, the high latent security level of the isotopic label can be shown through visual observation while getting a light absorption spectrum in the visible region, which plays the role similarly.

With the IR absorption method using a semiconductor laser, at least three kinds of light whose wavelengths are both in the infrared region and in the visible region generated by use of at least two semiconductor lasers are utilized and at least one peak in each of a vibration spectrum in the infrared region and a light absorption spectrum in the visible region is obtained. Where the wave number region 1 of the afore-indicated FIG. 1 is part of the vibration spectrum and the wave number region 2 is part of the light absorption spectrum in the visible region, the wave numbers of the light generated by the two semiconductor lasers are made in coincidence with the wave number regions 1 and 2, respectively, thereby enabling the substances having the light absorption spectra (a)~(c) in FIG. 1 to be identified from one another. Using information concerning at least one peak obtained in each of both regions, substances for the isotopic label are identified, respectively.

With the Raman scattering method, in addition to the vibration spectrum being obtained by detecting a Raman line by use of a semiconductor laser having a wave number (wavelength) in the visible region as an irradiation light source, at least three kinds of light having different wave numbers (wavelengths) are generated by the use of the semiconductor laser, and the beams are irradiated on the substances for an isotopic label to measure the intensity of transmitted light, scattered light or reflected light, thereby obtaining at least one peak of the light absorption spectrum in the visible region. Using information concerning the resulting vibration spectrum and the at least one peak of the light absorption spectrum in the visible region, a substance for the isotopic label is identified.

Next, the thus obtained vibration spectrum is subjected to pattern recognition or is compared with a reference data by use of an isotopic label reader and is thus identified to read the isotopic label. The data of the obtained vibration spectra may be subjected to pattern recognition by use of the discrimination model prepared according to chemometrics. It will be noted that the term "chemometrics" is a newly coined word from the combination of chemistry and metrics, and is a technique which makes full use of mathematical and statistical techniques to maximize the amount of chemical information extracted from chemical data such as vibration spectra.

For the preparation of the discrimination model, a data set of a multitude of samples whose classes to be sorted have been identified beforehand is used. The wave number of vibration spectrum is taken as an explaining variable and the strength is taken as its value, and a discrimination model in a technique such as KNN (K nearest neighbor) or SIMCA (soft independent modeling of class analogy) or the like is constructed and optimized. Using such a discrimination model as prepared beforehand, the class of an actually obtained vibration spectrum can be identified or sorted.

It will be noted that a method of identifying a printed matter has been already proposed (Japanese Laid-open Patent Application No. H10-149473), in which a resin or pigment forming a printed matter is identified by use of a slight difference in near infrared spectrum. In the invention of the Japanese Laid-open Patent Application No. H10-149473, a slight difference in the vibration spectrum of a material used is utilized. In contrast, according to the invention, a material having a specific vibration spectrum is positively used as a label, thereby ensuring reliable construction of a discrimination model of a higher discrimination or identification capacity.

Preferred Examples of Isotopically Labeling Substances for Nondestructive Reading In the practice of the invention, an isotopic label for nondestructive reading is attached to an article beforehand. The preferred substances of the invention constituting the isotopic label for nondestructive reading should contain at least one element having a plurality of stable isotopes, should include one substance wherein a content ratio of at least one stable isotope of the plural isotopes is so controlled as to be not higher than a natural isotopic abundance ratio and another substance wherein a content ratio of the stable isotope is so controlled as to be not lower than the natural isotopic abundance ratio, and should have a vibration spectrum which differs from the vibration spectrum of the substance having a content ratio of the stable isotope of the constituent element equal to the natural isotopic abundance ratio. Both substances, i.e. a substance containing at least one stable isotope having a plurality of stable isotopes with a content ratio of at least one stable isotope selected there among being not higher than the natural isotopic abundance ratio and a substance wherein the content ratio of the stable isotope is not lower than the natural isotopic abundance ratio, are same in the chemical structure thereof but have the content ratios of the stable isotope of the element which, respectively, differ from the natural isotopic abundance ratios. Both are applied to by an appropriate technique including (1) attachment to an article as a mixture, and (2) attachment of either of them to an article and the other put thereon.

Other preferred substances constituting the isotopic label for nondestructive reading are those substances wherein with respect to at least two elements selected from hydrogen, carbon, nitrogen and oxygen, the content ratios of the stable isotopes thereof are so controlled as to differ from natural isotopic abundance ratios, respectively, and vibration spectra differ from a vibration spectrum of a substance having content ratios of the stable isotopes of the constituent elements equal to the natural isotopic abundance ratios, respectively. In this connection, it is preferred that the substances should not have stable isotopes in constituent elements other than hydrogen, carbon, nitrogen and oxygen. As having stated hereinbefore, if elements other than the specified elements of a labeling substance have stable isotopes, part of the effect expected from the elements whose ratios of stable isotopes are controlled may be counteracted in some case.

Preferred examples of the substance of the isotopic label are those substances which are in the form of a stable solid at normal temperature and normal pressure. Examples include urea, glycine, leucine, alanine, glucose, ammonium nitrate, ammonium acetate, ammonium phosphate, sodium phosphate, benzamide, sodium nitrate, diphenyl, dicyclohexane, benzoic acid, sodium acetate, sodium carbonate, sodium hydrogencarbonate, sodium propionate, sodium formate, sodium octanoate, sodium glutamate, phthalimide, valine, sodium octanoate, sodium palmitate and the like.

Other preferred examples of the substance for the isotopic label include dyes. The dye used herein should be broadly interpreted and means pigments and dyestuffs included within the category thereof. Those dyes are preferably used, in which a light absorption spectrum in the visible region is equal to that of a dye having content ratios of stable isotopes in elements equal to the natural isotopic abundance ratios (as stated hereinbefore, the vibration spectrum obtained by irradiation of light in the visible region suffers little influence of the content ratio of a stable isotope), but a vibration spectrum in the infrared region differs from that of a dye wherein content ratios of stable isotopes in elements are equal to the natural isotopic abundance ratios. Examples of the dye include phthalocyanine, indigo, aniline black, magenta, methyl violet, azo methine, quinacridone, and the like.

Applications of an Isotopic Label for Nondestructive Reading

The purposes in end use of an isotopic label according to the invention include, aside from (1) the judgment of authenticity, (2) identification, (3) quality certificate, (4) copyright protection, (5) determination of a stolen article, (6) logistics, (7) stock control, and the like. The label used herein means one which is attached to for the purposes of (1)~(7) above and allied purposes. More particularly, according to the invention, the isotopic label can be widely used in the fields where it is attached to an article and its information is read. Accordingly, the article attached with the isotopic label of the invention is not limited so far as the attachment of the label is necessary for these purposes. Although mutually overlapped examples may be mentioned because of the classification based on the purpose or shape, examples of (1)~(6) below can be indicated.

(1) For exchange tickets, paper currency, stamp, postage stamp, exchange coupon, bond, stock, bill, check, security or policy, book coupon and the like, (2) for brand name goods, bags, ornamental articles, articles of clothing, watches or clocks, rings, necklaces, cars and the like, (3) for objects for copyright protection, CD, optical disk, software for computer and the like, (4) for jewelry and noble metals, coin, noble metal bullion, badge of company, tag, picture, fine art, used item of prominent figure, medicine and the like, (5) for sheets, passport, various licenses, ID card, name card, ticket for spectator sports, ticket for theatre, prescription, medical certificate, inspection tag, official document and the like, and (6) for cards, credit card, telephone card, ticket or card used in mass transit such as by railway or bus, highway card, card for pachinko and the like software-built in cards, and the like.

The type of material for the sheets per se is not limited and hard paper and the like various types of paper are ordinarily used along with plastics. The type of material for the cards per se is not limited, and various types of materials may be used including, aside from synthetic resins such as acrylic resins, polyester resins, polyolefin resins (including polyvinyl chloride and the like), polyamide resins, polyurethane resins, polycarbonate resins and the like, metals such as aluminium (including alloys thereof), paper and the like.

EXAMPLES

The invention is described in more detail by way of examples including applications thereof, which should not be construed as limiting the invention thereto. In the following, the symbols of M, M1~M3, and the M-shaped form indicated in "Principle of nondestructive reading of isotopic label" are used for illustration.

Example 1

This example is one wherein sodium formate (HCOONa) was used as substance M constituting an isotopic label. Among the constituent elements of sodium formate, carbon C has two types of stable isotopes of $^{12}C$ and $^{13}C$. By synthesizing "substances wherein the content ratios of stable isotopes of constituent elements other than carbon are equal to the natural isotopic abundance ratios, respectively, and the content ratios of the stable isotopes alone of carbon are appropriately controlled", sodium formate substances corresponding to the substances M1~M3, respectively, can be obtained. Sodium formate having a stable isotope ratio corresponding to the natural isotopic abundance ratio was used as a substance corresponding to substance M1. Artificially synthesized sodium formate wherein a content ratio of $^{12}$C is at 1% was provided as one corresponding to substance M2, i.e. sodium formate wherein the content ratio of $^{12}$C is significantly lower than the content ratio of $^{13}$C. Sodium formate which consists of a mixture of M1 and M2 in equal amounts (by weight) was provided as one corresponding to substance M3. It will be noted that among the constituent elements of the substance, Na is an element having no stable isotope.

Figure 7:
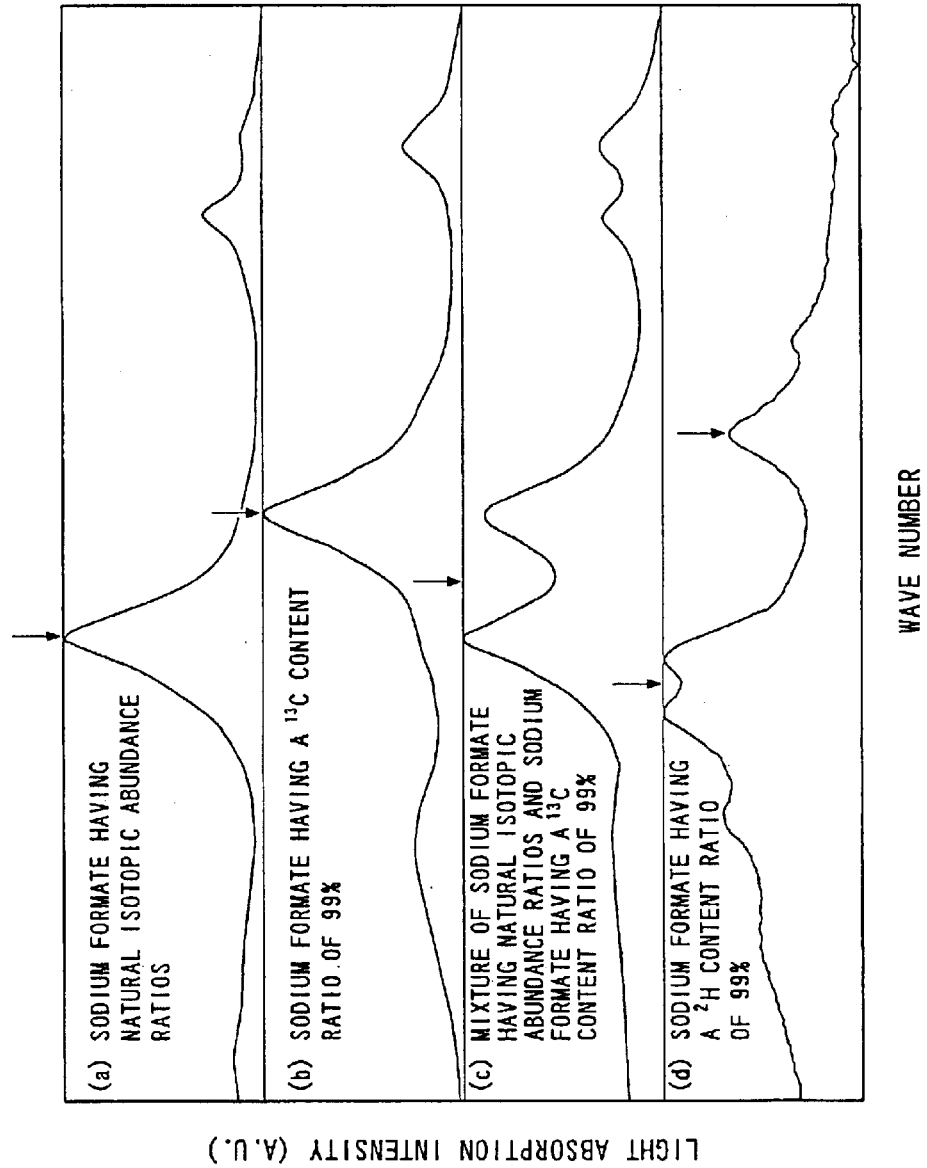
FIG. 7 is a view showing the results of Example 1.

The powders of the three types of sodium formate were each diluted with a potassium bromide powder to 5 wt %, and each was applied onto the surface of a plastic card (vinyl chloride resin), followed by coverage of the surface with a silicon thin sheet and measurement of a vibration spectrum according to a diffuse reflection method. FIGS. 7(a)~(c) are, respectively, a view showing part of the results based on the actual measurements. In FIG. 7, peaks indicted by the arrows (↓) differ from one another. As shown in FIG. 7(c), with the mixture in equal amounts corresponding to substance M3, a M-shaped spectrum is contained. In this way, three types of sodium formate can be distinctly discriminated from one another by measuring vibration spectra within a specific wave number region (wavelength region), and can thus be used as a constituent substance of an isotopic label carrying information, respectively. In wave number regions other than those shown in FIGS. 7(a)~(c), six or more peaks which can be used for the discrimination can be confirmed.

Therefore, as for sodium formate, the form of sodium formate with the natural isotopic abundance ratio of carbon is close to one corresponding to substance M1, and thus those forms corresponding to substances M2 and M3 have high rarity and can be used as constituent substances for isotopic labels that are difficult to forge.

FIG. 7(d) shows the results of measurement of a vibration spectrum of sodium formate of the type wherein the ratio of the stable isotopes of hydrogen was controlled at $^1$H:$^2$H ($^2$H=D)=1:99 and the content ratios of stable isotopes of the constituent elements other than hydrogen were coincident with the natural isotopic abundance ratios, respectively. The sodium formate of FIG. 7(a) has the natural isotopic abundance ratio of hydrogen, $^1$H:$^2$H ($^2$H=D)=99.985:0.015, and the peaks of FIGS. 7(a) and (d), indicated by the arrows, differ from each other. Thus, the two types of sodium formate can be distinctly discriminated from each other by measuring the vibration spectra within the specific wave number region (wavelength region) and can be used as constituent substances for information-carrying labels, respectively.

Example 2

Figure 8:
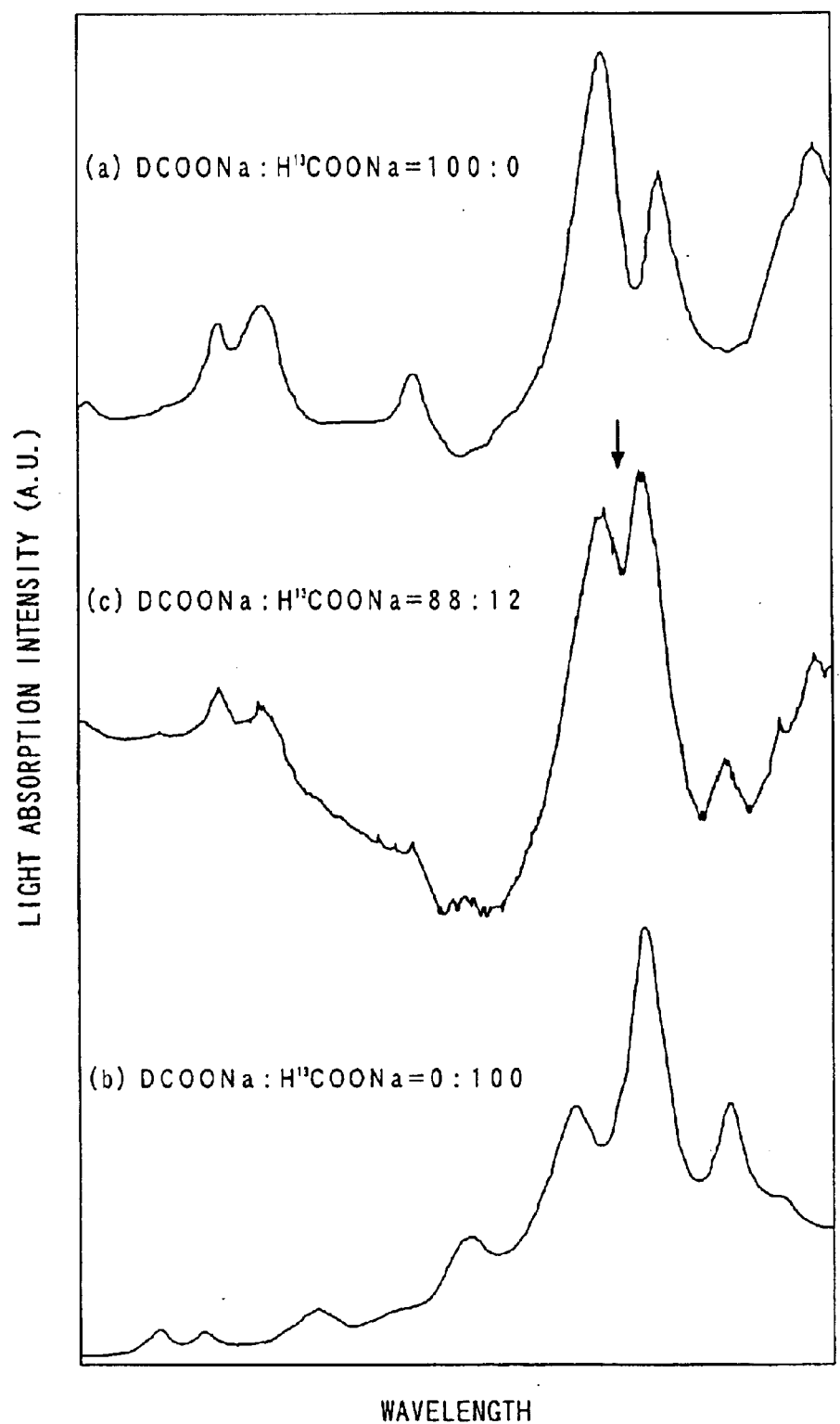
FIG. 8 is a view showing the results of Example 2.

Two types of sodium formate, each controlled in a content ratio of stable isotopes, (both were solid at normal temperature and normal pressure and were used as a powder in this experiment), and a mixture of the two types of sodium formate were, respectively, subjected to nondestructive measurement of a vibration spectrum in near infrared region by using an infrared absorption method with an acousto-optical tunable filter. FIG. 8 is a view showing the results of the measurement wherein the vertical axis shows light absorption intensity (arbitrary unit=A.U.) and the horizontal axis shows wavelength. In FIG. 8,(a) indicates a light absorption spectrum of sodium formate (represented by DCOONa) wherein the content ratio of stable isotopes of hydrogen was controlled to be $^1$H:$^2$H ($^2$H=D)=1:99, (b) indicates a light absorption spectrum of sodium formate (represented by H$^{13}$COONa) wherein the content ratio of stable isotopes of carbon was controlled to be $^{12}$C:$^{13}$C=1:99, and (c) indicates a light absorption spectrum of a mixture containing 88 wt % of DCOONa and 12 wt % of H$^{13}$COONa. As shown in FIGS. 8(a)~(c), the light absorption spectrum (c) of the mixture of the two types of sodium formate, i.e. a mixture of two types of sodium formate wherein the content ratios of the stable isotopes of hydrogen and carbon are, respectively, controlled, apparently differs from those of sodium formate (a) and (b) wherein the content ratio of stable isotopes of one type of element is controlled. In FIG. 8, the portion indicated by the arrow (↓) indicates the afore-mentioned, artificially introduced M-shaped light absorption spectrum. This mixture is more rare than the substance wherein the content of stable isotopes of one type of elements is controlled and can be used as a constituent substance for isotopic labels that is more difficult to forge.

Example 3

Figure 9:
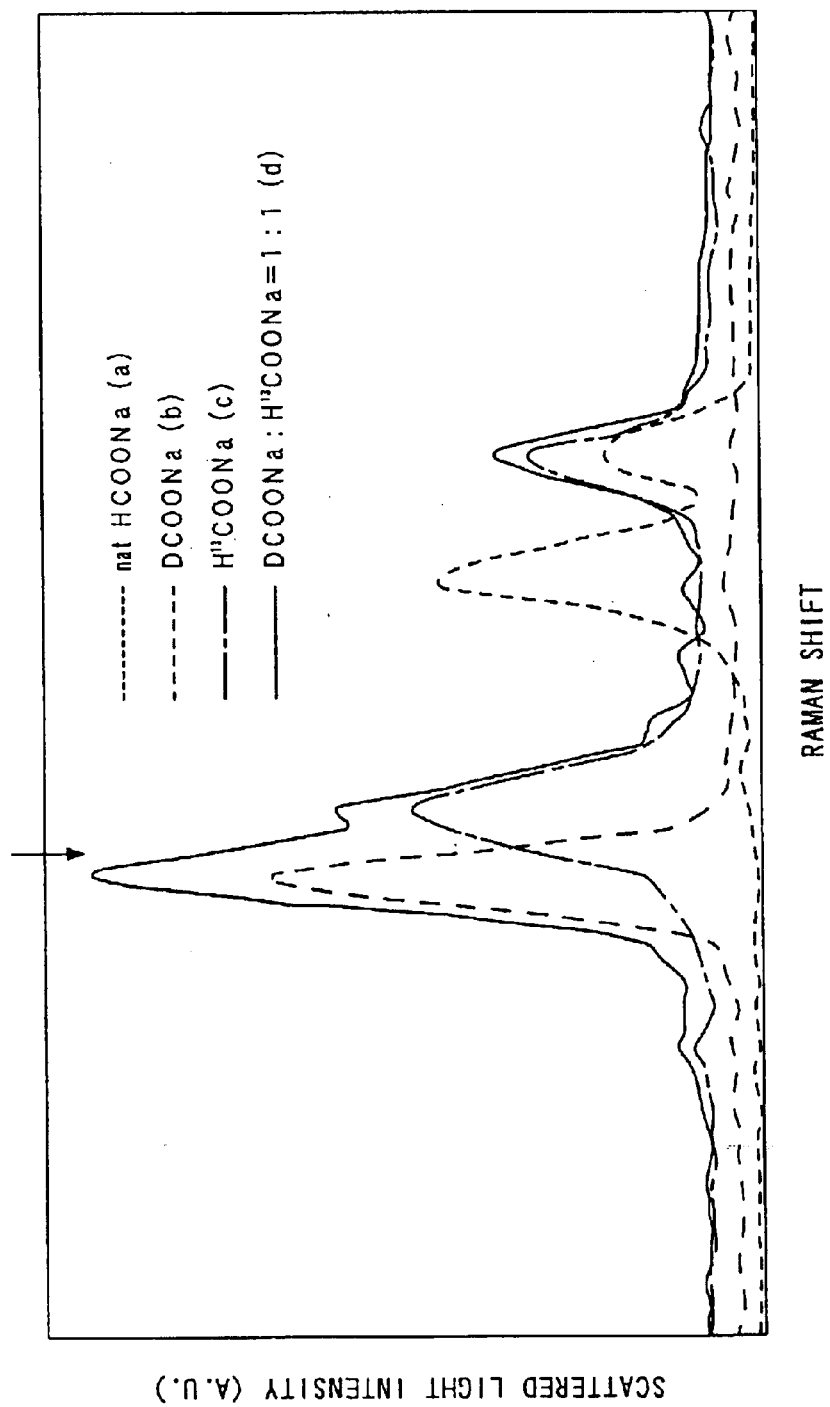
FIG. 9 is a view showing the results of Example 3.

Sodium formate wherein the content ratio of stable isotopes of hydrogen was controlled, sodium formate wherein the content ratio of stable isotopes of carbon was controlled (both were solid at normal temperature and normal pressure and were used as a powder in this experiment, respectively), and a mixture of these two types of sodium formate were each subjected to nondestructive measurement of a vibration spectrum by using a Raman scattering method. FIG. 9 is a view showing the results wherein the vertical axis shows scattered light intensity (arbitrary unit=A.U.) and horizontal axis shows Raman shift. In FIG. 9,(a) indicates the scattered light intensity of sodium formate (indicated by natHCOONa) with the natural isotopic abundance ratios, (b) indicates a scattered light intensity of sodium formate (indicated by DCOONa) wherein the content ratio of stable isotopes of hydrogen is controlled such that $^1$H:$^2$H ($^2$H=D)= 1:99, (c) indicates the scattered light intensity of sodium formate (indicated by H$^{13}$COONa) wherein the content ratio of stable isotopes of carbon is controlled to be $^{12}$C:$^{13}$C=1:99, and (d) indicates the scattered light intensity of a mixture of 50 wt % of the DCOONa and 50 wt % of the H$^{13}$COONa.

As shown in FIGS. 9(a)~(d), the Raman spectrum (d) of the mixture of the two types of sodium formate, i.e. a mixture of two types of sodium formate wherein the content ratios of stable isotopes of hydrogen and carbon are, respectively, controlled, apparently differs from those Raman spectra (a)~(c) of the other three types of sodium formate. In FIG. 9, the artificially introduced M-shaped Raman spectrum appears at the portion indicated by the arrow (↓). The mixture is more rare than the other three substances and can be used as a constituent substance for isotopic labels that are more difficult to forge.

Example 4

Figure 10:
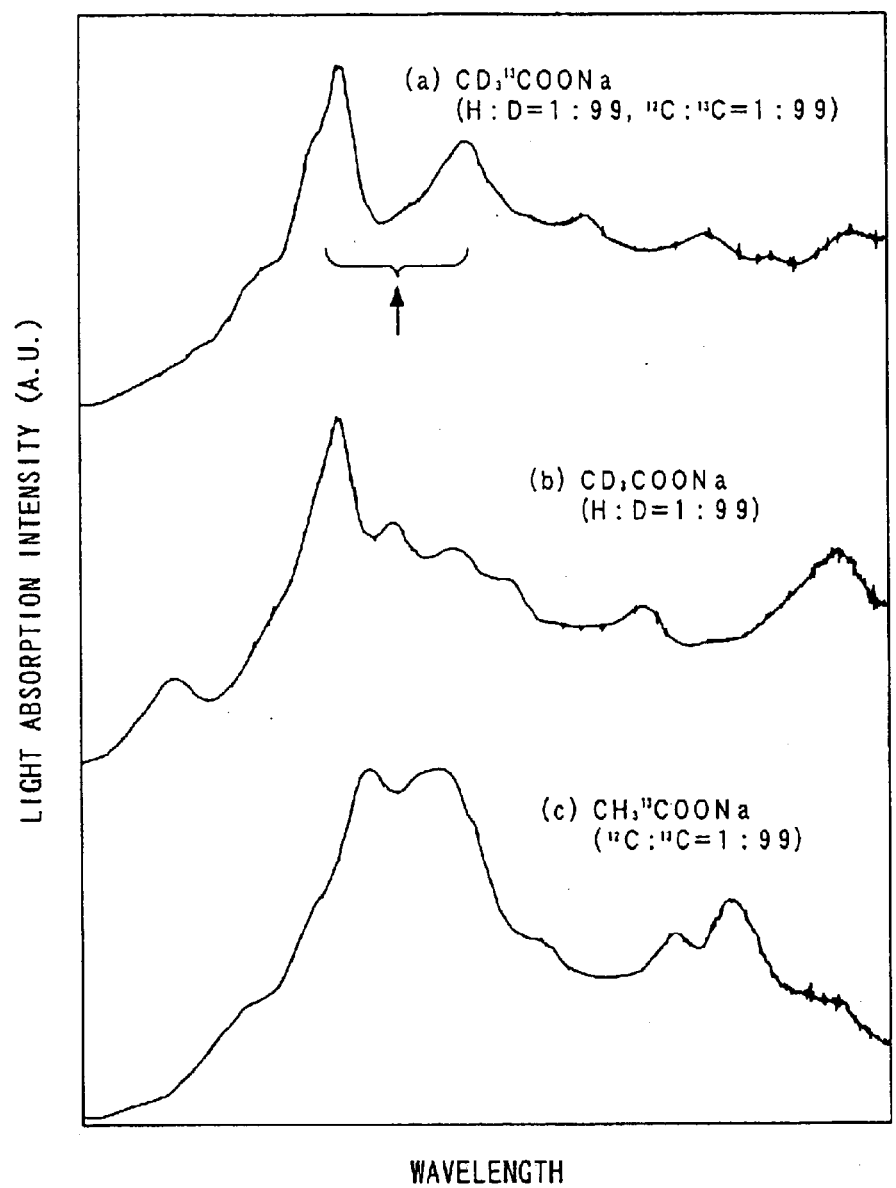
FIG. 10 is a view showing the results of Example 4.

In this example, sodium acetate substances wherein the content ratios of two stable isotopes of each of hydrogen and carbon were controlled (both were solid at normal temperature and normal pressure and were used as a powder in this experiment) were used as constituent substance of an isotopic label of the invention and were subjected to nondestructive measurement of a light absorption spectrum in near infrared region by using an infrared absorption method with an acousto-optic tunable filter. FIG. 10 is a view showing the results of the measurement wherein the vertical axis shows light absorption intensity (arbitrary unit=A.U.) and the horizontal axis shows wavelength. In FIG. 10,(a) indicates a light absorption spectrum of sodium acetate (indicated by CD$_3$$^{13}$COONa) wherein the content ratio of stable isotopes of hydrogen was controlled to be $^1H:^2H$ $(^2H=D)=1:99$ and the content ratio of stable isotopes of carbon was controlled to be $^{12}C:^{13}C=1:99$. (b) indicates a light absorption spectrum of sodium acetate ($CD_3COONa$) wherein the content ratio of stable isotopes of hydrogen was controlled to be $^1H:^2H$ $(^2H=D)=1:99$. (c) indicates a light absorption spectrum of sodium acetate ($CH_3^{13}COONa$) wherein the content ratio of stable isotopes of carbon was controlled to be $^{12}C:^{13}C=1:99$.

As shown in FIGS. 10(a)~(c), the light absorption spectrum (a) of sodium acetate ($CH_3^{13}COONa$) wherein the content ratios of stable isotopes of both of hydrogen and carbon were controlled apparently differs from those light absorption spectra (b) and (c) of the sodium acetate substances wherein the content ratio of stable isotopes of either of hydrogen or carbon was controlled. In FIG. 10, the portion indicated by the arrow (↑) is the afore-mentioned artificially introduced M-shaped light absorption spectrum. This substance can be used as a constituent substance for isotopic labels which has more rarity and are more difficult to forge.

Example 5

This example illustrates the use of urea $[CO(NH_2)_2]$ as substance M for isotopic labels. Among the constituent elements of urea, hydrogen H has two types of stable isotopes of $^1H$ and $^2H$, with the natural isotopic abundance thereof being at 99.985% for $^1H$ and at 0.015% for $^2H$ (=D). When "a substance wherein the isotopic content ratios of the constituent elements other than hydrogen are, respectively, equal to the natural isotopic abundances and only the isotopic content ratio of hydrogen is controlled", i.e. urea wherein only the isotopic content ratio of hydrogen differs from the natural isotopic abundance ratio (or is controlled), is synthesized, urea substances corresponding to the afore-indicated M1~M3 can be obtained. For substance M1, urea of the type wherein the content ratio of $^1H$ is significantly higher than the content ratio of $^2H$ is used. For substance M2, urea of the type wherein the content ratio of $^1H$ is significantly lower than the content ratio of $^2H$ is used. For substance M3, a urea mixture of these substances substantially in equal amounts is used. This means that the natural form of urea is close to that corresponding to substance M1, and those substances corresponding to substances M2 and M3, respectively, have high rarity and can be used as constituent substances for isotopic labels that is difficult to forge.

Among the constituent elements of urea, nitrogen N has two types of stable isotopes of $^{14}N$ and $^{15}N$, with their natural isotopic abundance being at 99.63% for $^{14}N$ and at 0.366% for $^{15}N$. By synthesizing "a substance wherein the isotopic content ratios of the constituent elements other than nitrogen are, respectively, equal to the natural isotopic abundance ratios and only the isotopic content ratio of nitrogen is controlled", i.e. urea wherein only the isotopic content ratio of nitrogen differs from the natural isotopic abundance ratio, urea substances corresponding to substances M1~M3 can be obtained, like the case of hydrogen. Moreover, with respect to carbon C selected among the constituent elements of urea, urea substances corresponding to substances M1~M3 can be obtained in a similar way.

Figure 11:
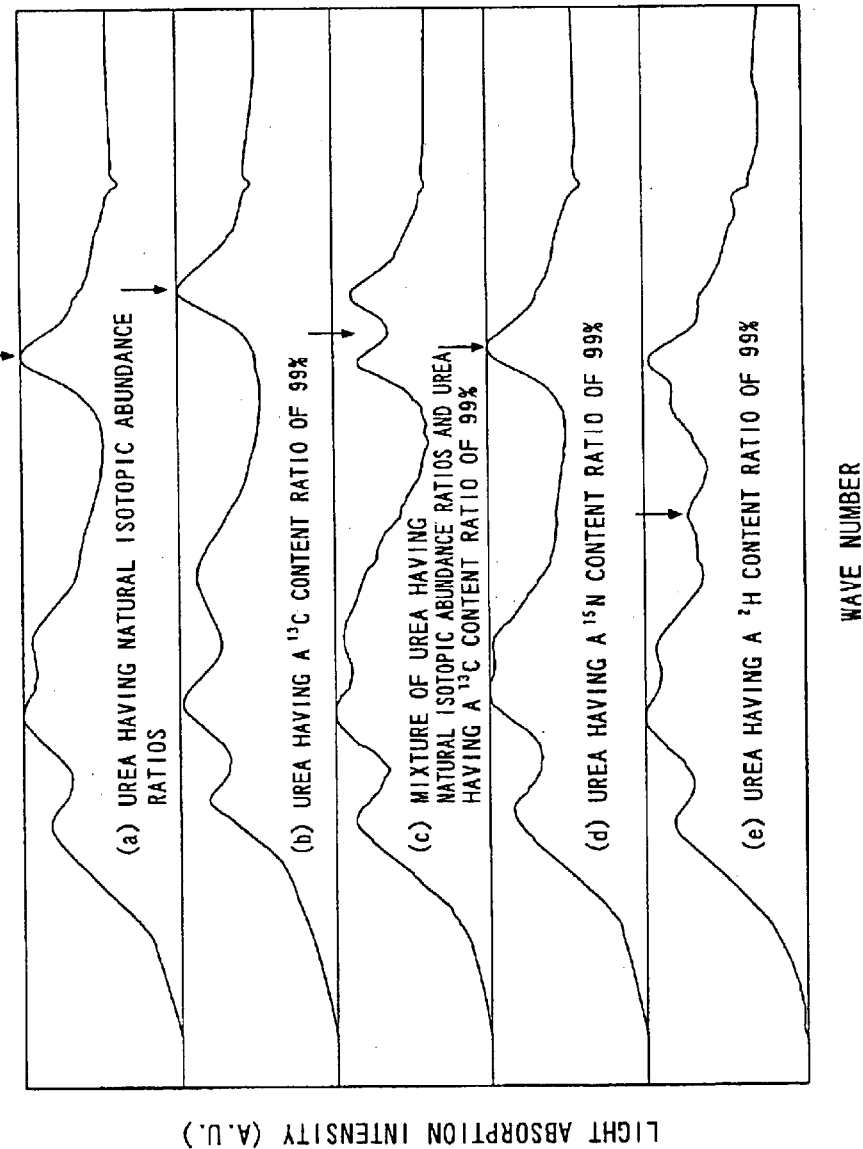
FIG. 11 is a view showing the results of Example 5.

FIG. 11 is a view showing part of a vibration spectrum of each of the following samples (a)~(e), wherein about 2 mg of individual samples was attached to an aluminium sheet, covered with a silicon thin sheet and subjected to a diffuse reflection method to obtain a vibration spectrum based on the resultant actual measurement. In FIG. 11, the vertical axis shows light absorption intensity [arbitrary unit=A.U.] and the horizontal axis shows wave number.

(a) Urea having the natural isotopic abundance ratios.
(b) A sample obtained by diluting artificially synthesized urea, which has a content ratio of $^{12}C$ of 1% considerably lower than the content ratio of $^{13}C$, with powders of potassium bromide to 5 wt %.
(c) A mixture sample obtained by mixing (a) and (b) above in equal amounts (by weight).
(d) A sample obtained by diluting artificially synthesized urea, which has a content ratio of $^{14}N$ of 1% considerably lower than the content ratio of $^{15}N$, with powders of potassium bromide to 5 wt %.
(e) A sample obtained by diluting artificially synthesized urea, which has a content ratio of $^1H$ of 1% considerably lower than the content ratio of $^2H$, with powders of potassium bromide to 5 wt %.

As shown in FIGS. 11(a)~(e), the peaks indicated by the respective arrows (↓) differ from one another. When the vibration spectra within the respective wave number regions (wavelength regions) including these peaks are obtained, these substances can be discriminated from one another. Within wave number regions other than the regions indicated in FIG. 11, five or more peaks which could be used for the discrimination were confirmed.

An artificially formed M-shaped peak appears at the portion indicated by the arrow (↓) of FIG. 11(c). It will be noted that with respect to FIG. 11, a technique using a label code wherein the content ratio of $^{13}C$ is higher than the natural abundance ratio has been already developed (Japanese Laid-open Patent Application No.H10-287075). In the practice of the invention, the artificial realization of the M-shaped vibration spectrum ensures the provision of an isotopic label which is difficult to forge and exhibits a higher security level.

Example 6

This example illustrates an instance wherein in (a) of FIG. 2 showing the attachment of an isotopic label, the dye used at character A is made of a dye whose light absorption spectrum in the visible region is equal to that of a natural dye but differs from that of the natural dye with respect to the vibration spectrum in the infrared region, and the natural dye is used at characters B, C. The character portion of A and the character portions of B, C seem to have the same color through visual observation. However, when vibration spectra in the infrared region are obtained, the true isotopic label indicates that the vibration spectrum of the character portion of A alone is different from that of the natural dye.

As stated hereinabove, a dye wherein the content ratio of stable isotopes of a constituent element can be used as a substance for isotopic labels. A dye can be synthesized for use as a substance for an isotopic label by controlling the content ratio or ratios of stable isotopes of one or more constituent elements of raw materials. By selecting the type and structural position of an element, among constituent elements of raw materials, which is controlled in the content ratio of stable isotopes thereof, there can be synthesized a dye which is equal to an ordinarily prepared dye with respect to the absorption, reflection and transmission characteristics in the visible region but differs therefrom with respect to the vibration spectrum in the infrared region. This enables one to realize a isotopic label constituting substance which cannot be distinguished from ordinary dyes through visual judgment but can be judged for the first time as an isotopic label constituting substance upon measurement of absorption, reflection or transmission characteristics within a specific wave length region (wave number region) and is thus high in security level.

Specific Example 1 of a Dye Substance for Isotopic Label: Phthalocyanine

This is a substance which is obtained by heating phthalic anhydride (or phthalimide) and a metal salt in urea melt. When the content ratio of stable isotopes of carbon C, nitrogen N or hydrogen H which is a constituent element of starting urea or phthalic anhydride (or phthalimide) is controlled, the content ratio of the stable isotopes of the constituent element in the resulting phthalocyanine can be controlled. When a copper salt is used as the metal salt, a blue dye is obtained, and when a chlorine atom is arranged at the benzene ring, a green dye is obtained.

Specific Example 2 of a Dye Substance for Isotopic Label: Indigo

This is a blue dye. After addition of formaldehyde and sodium cyanide (or potassium cyanide) to aniline, sodium hydroxide is added to, thereby preparing N-phenylglycine, followed by dehydration reaction to prepare indoxyl. This is oxidized in an alkaline solution or oxidized in air to obtain indigo. When the content ratio of stable isotopes of carbon C, nitrogen N, oxygen O or hydrogen H, which is a constituent element of starting aniline, formaldehyde, sodium cyanide (potassium cyanide) or sodium hydroxide, is controlled, the stable isotope content ratio of the constituent element of the synthesized indigo can be controlled.

Specific Example 3 of a Dye Substance for Isotopic Label: Aniline Black

This is a black dye obtained by oxidative condensation of aniline. An aqueous solution of aniline hydrochloride and an oxidizing agent (dichromic acid or sodium chlorate) is heated to cause an oxidation condensation reaction. When the stable isotope content ratio of carbon C, nitrogen N or hydrogen H which is a constituent element of the starting aniline is controlled, the stable isotope content ratio of the constituent element of the resulting aniline black can be controlled.

Specific Example 4 of a Dye Substance for Isotopic Label: Magenta

This is a reddish purple dye obtained by oxidative condensation of hydrochloride compounds of aniline, p-toluidine and o-toluidine with nitrobenzene. When the stable isotope content ratio of carbon C, nitrogen N or hydrogen H which is a constituent element of the starting hydrochloride compounds of aniline, p-toluidine and o-toluidine is controlled, the stable isotope content ratio of the constituent element of the resulting magenta can be controlled.

Specific Example 5 of a Dye Substance for Isotopic Label: Methyl Violet

This is a bluish purple dye prepared by heating a mixture of dimethylaniline, phenol, copper sulfate, sodium chloride and water for oxidative condensation of the dimethyl aniline via air. When the stable isotope content ratio of carbon C, nitrogen N or hydrogen H which is a constituent element of the starting dimethylaniline or phenol is controlled, the stable isotope content ratio of the constituent element of the resulting methyl violet can be controlled.

Specific Example 6 of a Dye Substance for Isotopic Label: Azo Methine

This is a yellow dye prepared by heating, for condensation, an aniline derivative (such as aminoaniline or the like) and an aldehyde derivative (nitrobenzaldehyde or the like) in an alcohol in the presence of a small amount of an acid. When the stable isotope content ratio of carbon C, nitrogen N, oxygen O or hydrogen H which is a constituent element of the starting aniline derivative or aldehyde derivative is controlled, the stable isotope content ratio of the constituent element of the resulting azo methine can be controlled.

Specific Example 7 of a Dye Substance for Isotopic Label: Quinacridone

Aniline and diethyl-2,5-hydroxy-1,4-cyclohexadiene-1,4-dicarboxylate are provided as starting material to obtain a red dye through intramolecular ring-closing reaction. When the content ratio of stable isotopes of carbon C, nitrogen N, oxygen O or hydrogen H serving as a constituent element of the starting materials is controlled, the content ratio of the stable isotopes of the constituent element in the resultant quinacridone can be controlled.

Example 7

This example is one wherein the vibration spectrum of an isotopic label is read to judge the authenticity of an article attached with the isotopic label based on the results of the reading. The system used in the present invention includes, for instance, a device for reading and obtaining a vibration spectrum, a device for reading an isotopic label by subjecting the data of the vibration spectrum to pattern recognition, and a device for judging the authenticity of an article through information of the isotopic label.

The respective devices may be not only those which are set at one position, but also those wherein one or plural devices are separately located and mutually connected with one another through a communication network. The communication network includes, aside from a telephone communication network, at least one of an internet and an intranet. This ensures not only individual devices being not limited with respect to the installation location and the geographical site, but also the possibility of control from a remote area or the designation of control parameters from a remote area. For instance, using a control device at a remote area, the operations of the respective devices including the designation of an isotopic label attaching position where data is to be obtained by a vibration spectrum measuring device, the selection of a judgment model used in an isotopic label reading device, the judgment logic of a device of judging authenticity and the like may be altered or renewed depending on the circumstances, if necessary, while working the system.

Figure 12:
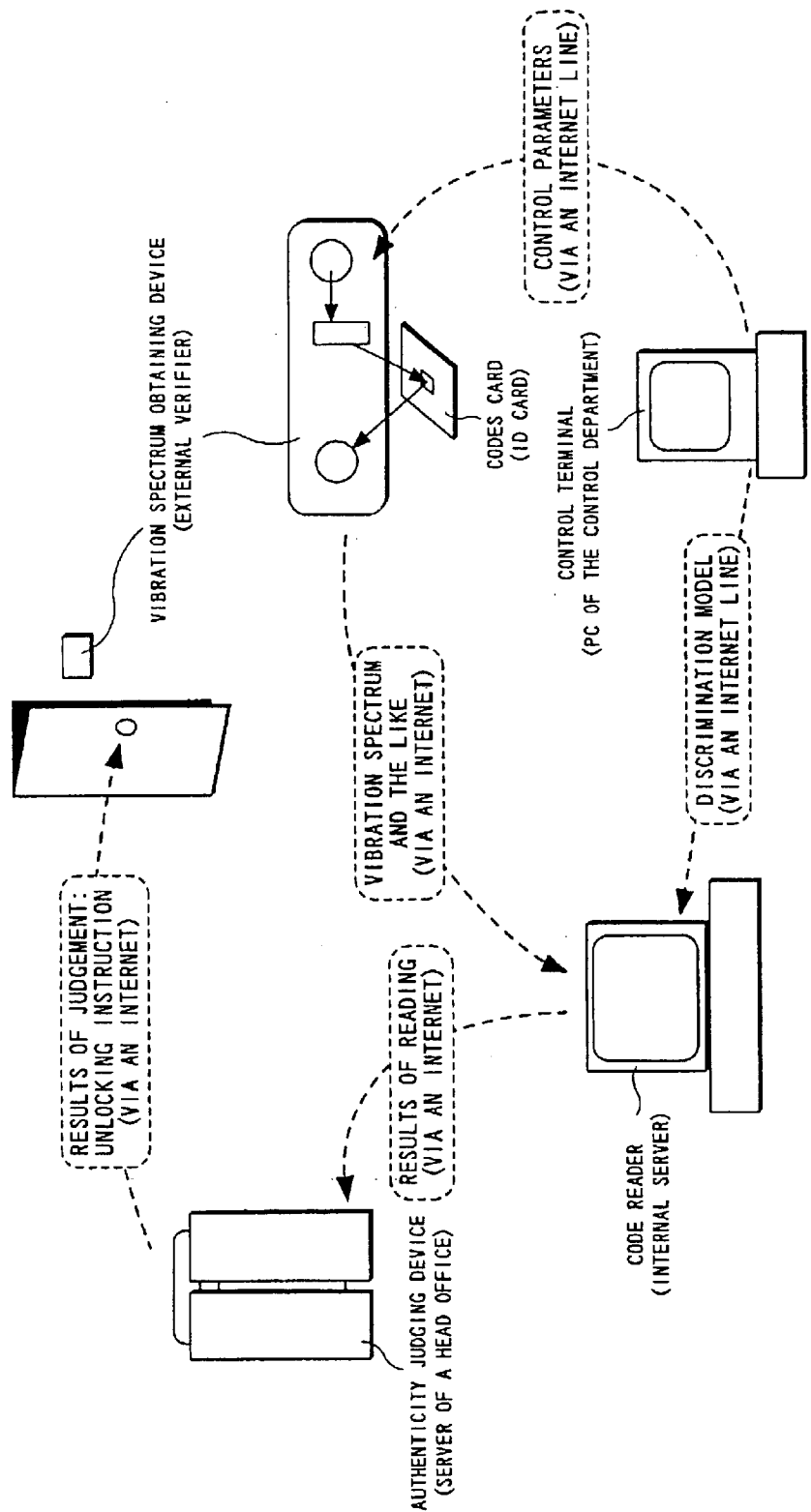
FIG. 12 is a view showing an application of the invention to admission authentication using a communication network in Example 7.

FIG. 12 is an application of the invention to a card verifier using a communication network. In order that one opens the door from outside of a building and enters into the building, a card (ID card) attached with an isotopic label has to be inserted into a vibration spectrum obtaining device (i.e. an external verifier). This permits data to be obtained with respect to the vibration spectrum of the isotopic label constituting substance attached to the card, time and the like. Next, these data are transferred to an isotopic label reading device (an inside server) via an intranet and subjected to pattern recognition for reading as an isotopic label. For instance, the isotopic label attached to the card reveals that the person inserting the card may be recognized as an employee belonging to the department in the building, an employee in other department, an employee of a related company, VIP, a person on the blacklist or the like. The results of the recognition are transferred to an authenticity judging device (i.e. a server of a head office) via an internet thereby judging the authenticity of the inserted card.

If the card is judged as true, instructions are issued via the internet so as to execute the preset operations for every result of recognition. For instance, where recognized as an employee belonging to the department in the building, the door is unlocked, and where recognized as an employee of a related company, VIP or a person on the blacklist, a predetermined message is sent to a preliminarily designated person in charge simultaneously with the door being unlocked. On the other hand, when judged as false, no unlocking instruction is issued on the door. In this case, it is possible to preliminarily designate the option that the warning buzzer set near the door is on.

A series of control parameters including the position of attaching an isotopic label to be read can be designated by transfer from a control terminal to a vibration spectrum obtaining device via an internal line. This function becomes necessary in case where a plurality of isotopic labels are attached to an ID card for improving a security level. A more elaborated judging model is developed while taking into account the existing circumstances of forgery and is transferred to the isotopic label reader via an internal line to update a discrimination model.

The isotopic label discrimination system set forth hereinabove can be applied to a method of nondestructively judging the authenticity of an article. More particularly, because a substance constituting the isotopic label has an inherent vibration spectrum which does not ordinarily exist in a natural field, it is possible to determine whether or not an article is true or false in high precision depending on the conformity or inconformity with the vibration spectrum. The detecting method, valuation conditions and judging conditions can be simultaneously set from outside through a communication, so that maintenance is simpler than that of an existing ROM type and the effect of preventing the leakage of determination standards is higher.

Moreover, the results of the judgment obtained in the above-stated evaluation data extraction mechanism, comparison mechanism with reference data, and results-judging mechanism can be stored in a memory along with additional data such as of days, times, and places, and thus can be used in various controls of articles on which an isotopic label has been attached. For instance, a substance for an isotopic label, a control number and the like are recorded, and the results of judgment are logged and stored in the memory of the isotopic label judging system along with the additional data such as of days and times and places. This leads to the discovery of the existence of a counterfeit other than the authentic by detecting the unnatural situation of tacking data of days, times and places, or the fact of alternate judgment, for example, in Hokkaido or Okinawa even if the results of judgment are same or articles are forged perfectly.

EFFECTS OF THE INVENTION

According to the invention, information of an isotopic label attached on an article beforehand can be read readily and quickly without destruction. Further, according to the invention, various excellent effects can be obtained including the judgment of authenticity of an article being made nondestructively and in high precision based on the obtained information. The isotopic label per se for nondestructive reading according to the invention is difficult to forge and falsify, so that the purpose of anti-counterfeiting or the like can be achieved reliably in high precision.

What is claimed is:

1. A method for nondestructive reading of an isotopic label on an article comprising
   a) the isotopic label made of substances which, respectively, have at least one constituent element having a plurality of stable isotopes and which include both a substance wherein a content ratio of at least one stable isotope of the constituent element is not higher than a natural isotopic abundance ratio, and another substance wherein a content ratio of the same stable isotope is not lower than the natural isotopic abundance ratio, and said substances having a vibration spectrum different from the vibration spectrum of the substance wherein all content ratios of the stable isotopes of the constituent elements are equal to the natural isotopic abundance ratios, respectively,
   b) attaching the isotopic label on the article beforehand, and
   c) obtaining the vibration spectrum of the substances for the isotopic label nondestructively.

2. A method for nondestructive reading of an isotopic label on an article comprising
   a) the isotopic label made of a substance which has at least two elements selected from hydrogen, carbon, nitrogen and oxygen with each of the content ratios of stable isotopes thereof controlled to be different from the natural isotopic abundance ratio and which has a vibration spectrum different from the vibration spectrum of the substance whose content ratios of stable isotopes of the constituent elements are, respectively, equal to the natural isotopic abundance ratios,
   b) attaching the isotopic label on the article beforehand, and
   c) obtaining the vibration spectrum of the substance for the isotopic label nondestructively.

3. A method for nondestructive reading of an isotopic label on an article comprising
   a) the isotopic label made of a substance, which has at least two elements selected from hydrogen, carbon, nitrogen and oxygen with each of the content ratios of stable isotopes thereof controlled to be different from the natural isotopic abundance ratio, which has a vibration spectrum different from the vibration spectrum of the substance whose content ratios of stable isotopes of the constituent elements are, respectively, equal to the natural isotopic abundance ratios, and wherein the constituent elements other than hydrogen, carbon, nitrogen and oxygen have no stable isotopes,
   b) attaching the isotopic label on the article beforehand, and
   c) obtaining the vibration spectrum of the substance for the isotopic label nondestructively.

4. A method for nondestructive reading of an isotopic label on an article according to claim 1, characterized in that the vibration spectrum of the substance or substances for said isotopic label is nondestructively obtained by an infrared absorption method.

5. A method for nondestructive reading of an isotopic label on an article according to claim 1, characterized in that the vibration spectrum of the substance or substances for said isotopic label is nondestructively obtained by an infrared absorption method and obtained by an attenuated total reflectance method.

6. A method for nondestructive reading of an isotopic label on an article according to claim 1, characterized in that the vibration spectrum of the substance or substances for said isotopic label is nondestructively obtained by an infrared absorption method and obtained by a diffuse reflection method.

7. A method for nondestructive reading of an isotopic label on an article according to claim 1, characterized in that the vibration spectrum of the substance or substances for said isotopic label is nondestructively obtained by use of an acousto-optical tunable filter.

8. A method for nondestructive reading of an isotopic label on an article according to claim 1, characterized in that the vibration spectrum of the substance or substances for said isotopic label is nondestructively obtained by a Raman scattering method.

9. A method for nondestructive reading of an isotopic label on an article according to claim 8, characterized in that the vibration spectrum nondestructively obtained by the Raman scattering method is a vibration spectrum obtained by use of a semiconductor laser as a laser beam source, and the isotopic label is identified by using, in combination, information of a light absorption spectrum obtained by use of the light with at least three kinds of wavelengths generated by said semiconductor laser.

10. A method for nondestructive reading of an isotopic label on an article according to claim 1, characterized in that the vibration spectrum of the substance or substances for said isotopic label is nondestructively obtained by means of light with at least three kinds of wavelengths generated by a semiconductor laser.

11. A method for nondestructive reading of an isotopic label on an article according to claim 10, characterized in that the vibration spectrum of the substance for said isotopic label is a vibration spectrum obtained by use of the light with at least three kinds of wavelengths generated by a semiconductor laser, which is used in combination of information of light absorption spectra obtained by use of the light with at least three kinds of wavelengths generated by another semiconductor laser.

12. A method for nondestructive reading of an isotopic label on an article according to claim 1, characterized in that data of the vibration spectrum obtained by the nondestructive method of said isotopic label are identified by subjecting to pattern recognition by use of a discrimination model made according to a multi-variate analysis in chemometrics.

13. A method for nondestructively judging authenticity of an article attached with an isotopic label thereon by use of a nondestructive reading method comprising
a) the isotopic label made of substances which, respectively, have at least one constituent element having a plurality of stable isotopes and which include both a substance wherein a content ratio of at least one stable isotope of the constituent element is not higher than the natural isotopic abundance ratio, and another substance wherein a content ratio of the same stable isotope is not lower than the natural isotopic abundance ratio, and said substances having a vibration spectrum different from the vibration spectrum of the substance wherein all content ratios of the stable isotopes of the constituent elements are equal to the natural isotopic abundance ratios, respectively,
b) attaching the isotopic label on the article beforehand,
c) obtaining the vibration spectrum of the substances for the isotopic label nondestructively, and
d) judging the authenticity of said article based on the thus obtained information.

14. A method for nondestructively judging authenticity of an article attached with an isotopic label thereon comprising
a) the isotopic label made of a substance which has at least two elements selected from hydrogen, carbon, nitrogen and oxygen with each of the content ratios of stable isotopes thereof controlled to be different from the natural isotopic abundance ratio and which has a vibration spectrum different from the vibration spectrum of the substance whose content ratios of stable isotopes of the constituent elements are, respectively, equal to the natural isotopic abundance ratios,
b) attaching the isotopic label on the article beforehand,
c) obtaining the vibration spectrum of the substance for the isotopic label, and
d) judging the authenticity of said article based on the thus obtained information.

15. A method for nondestructively judging authenticity of an article attached with an isotopic label thereon comprising
a) the isotopic label made of a substance, which has at least two elements selected from hydrogen, carbon, nitrogen and oxygen with each of the content ratios of stable isotopes thereof controlled to be different from the natural isotopic abundance ratio, which has a vibration spectrum different from the vibration spectrum of the substance whose content ratios of stable isotopes of the constituent elements are, respectively, equal to the natural isotopic abundance ratios, and wherein the constituent elements other than hydrogen, carbon, nitrogen and oxygen have no stable isotopes,
b) attaching the isotopic label on the article,
c) obtaining the vibration spectrum of the substance for the isotopic label nondestructively, and
d) judging authenticity of said article based on the thus obtained information.

16. A method for nondestructively judging authenticity of an article attached with an isotopic label thereon according to claim 13, characterized in that a vibration spectrum obtaining device, a device for reading information of the isotopic label by subjecting data of the vibration spectrum to pattern recognition and a device for judging authenticity of the articles are worked by connection via a communication network.

17. A method for nondestructively judging authenticity of an article attached with an isotopic label thereon according to claim 16, characterized in that said communication network includes at least one of a telephone communication network, an internet and an intranet.

18. A method for nondestructively judging authenticity of an article attached with an isotopic label thereon according to claim 16, characterized in that at least one of said vibration spectrum obtaining device, said device for reading information of the isotopic label by subjecting data of the vibration spectrum to pattern recognition and said device for judging authenticity of the article is controlled from a remote area or is designated with control parameters from a remote area.

19. An isotopic label for nondestructive reading which is attached on an article beforehand comprising substances constituting said isotopic label which, respectively, have at least one constituent element having a plurality of stable isotopes and which include both a substance wherein a content ratio of at least one stable isotope of the constituent element is not higher than a natural isotopic abundance and ratio and another substance wherein a content ratio of the same stable isotope is not lower than the natural isotopic abundance ratio, and said substances having a vibration spectrum different from the vibration spectrum of the substance wherein all content ratios of the stable isotopes of the constituent elements are equal to the natural isotopic abundance ratios, respectively.

20. An isotopic label for nondestructive reading which is attached on an article beforehand comprising a substance constituting said isotopic label which has at least two elements selected from hydrogen, carbon, nitrogen and oxygen with each of the content ratios of stable isotopes thereof being controlled to be different from the natural isotopic abundance ratio, and which has a vibration spectrum different from the vibration spectrum of the substance whose content ratios of stable isotopes of the constituent elements are equal to the natural isotopic abundance ratios, respectively.

21. An isotopic label for nondestructive reading which is attached on an article beforehand comprising a substance constituting said isotopic label which has at least two elements selected from hydrogen, carbon, nitrogen and oxygen with each of the content ratios of stable isotopes thereof being controlled to be different from the natural isotopic abundance ratio, which has a vibration spectrum different from the vibration spectrum of the substance whose content ratios of stable isotopes of the constituent elements are, respectively, equal to the natural isotopic abundance ratios, and wherein the constituent elements of said substance other than hydrogen, carbon, nitrogen and oxygen have no stable isotopes.

22. An isotopic label for nondestructive reading which is attached on an article beforehand according to claim 19, characterized in that the vibration spectrum of the substance for said isotopic label contains at least one M-shaped or W-shaped pattern, in which adjacent two peaks are partially superposed, at a portion different from the vibration spectrum of the substance having the content ratio or ratios of stable isotopes of the constituent elements equal to the natural isotopic abundance ratio or ratios, respectively.

23. An isotopic label for nondestructive reading according to claim 19, characterized in that said isotopic label has a form in which the substance or substances controlled in the stable isotope ratio of the constituent element or elements are attached to two or more places.

24. An isotopic label for nondestructive reading according to claim 19, characterized in that said isotopic label has a plurality of portions attached with the substance or substances controlled in the stable isotope ratio or ratios of the constituent element or elements and said substance or substances is arranged two-dimensionally.

25. An isotopic label for nondestructive reading according to claim 19, characterized in that the substance for said isotopic label consists of urea, glycine, leucine, alanine, glucose, ammonium nitrate, ammonium acetate, ammonium phosphate, sodium phosphate, benzamide, sodium nitrate, diphenyl, dicyclohexane, benzoic acid, sodium acetate, sodium carbonate, sodium hydrogen carbonate, sodium propionate, sodium formate, sodium octoate, sodium glutamate, phthalimide, valine, sodium octanoate, or sodium palmitate.

26. An isotopic label for nondestructive reading according to claim 19, characterized in that the substance for said isotopic label consists of a dye.

27. An isotopic label for nondestructive reading according to claim 19, characterized in that the substance for said isotopic label consists of a dye whose light absorption spectrum in the visible region is equal to the light absorption spectrum of the dye having content ratios of stable isotopes of the elements constituting the last-mentioned dye equal to the natural isotopic abundance ratios, respectively, and whose vibration spectrum in the infrared region differs from the vibration spectrum of the dye having content ratios of stable isotopes of the elements constituting the last-mentioned dye equal to the natural isotopic abundance ratios, respectively.

28. An isotopic label for nondestructive reading according to claim 19, characterized in that the substance for said isotopic label is a dye selected from phthalocyanine, indigo, aniline black, magenta, methyl violet, azo methine, and quinacridone.

* * * * *